(12) United States Patent
Canham et al.

(10) Patent No.: US 7,294,406 B2
(45) Date of Patent: Nov. 13, 2007

(54) MEDICAL FIBRES AND FABRICS

(75) Inventors: Leigh Canham, Worcestershire (GB); Roger Aston, Worcestershire (GB)

(73) Assignee: Psimedica Limited, Malvern, Worcestershire (GB)

(*) Notice: Subject to any disclaimer, the term of this patent is extended or adjusted under 35 U.S.C. 154(b) by 73 days.

(21) Appl. No.: 10/499,535

(22) PCT Filed: Dec. 20, 2002

(86) PCT No.: PCT/GB02/05853

§ 371 (c)(1),
(2), (4) Date: Jul. 15, 2004

(87) PCT Pub. No.: WO03/055534

PCT Pub. Date: Jul. 10, 2003

(65) Prior Publication Data

US 2005/0048859 A1    Mar. 3, 2005

(30) Foreign Application Priority Data

Dec. 21, 2001 (GB) .................. 0130608.3

(51) Int. Cl.
*D03D 15/00* (2006.01)
*D04B 1/14* (2006.01)

(52) U.S. Cl. .............. 428/446; 442/189; 442/301; 442/308; 442/340; 442/415

(58) Field of Classification Search .......... 442/189, 442/301, 198, 199, 308, 334, 335, 339, 361, 442/414, 415; 428/365, 372, 373
See application file for complete search history.

(56) References Cited

U.S. PATENT DOCUMENTS

| | | | |
|---|---|---|---|
| 5,053,248 A | | 10/1991 | Hakamata et al. |
| 5,126,200 A | * | 6/1992 | Nordine .................. 428/366 |
| 5,336,360 A | | 8/1994 | Nordine |
| 5,755,850 A | | 5/1998 | Martin et al. |
| 6,207,749 B1 | * | 3/2001 | Mayes et al. ............ 524/731 |

FOREIGN PATENT DOCUMENTS

| | | |
|---|---|---|
| EP | 0 960 600 A1 | 12/1999 |
| GB | 2 255 281 A | 11/1992 |
| GB | 2 317 885 A | 4/1998 |

(Continued)

OTHER PUBLICATIONS

Maeda et al., Silicon Nanostructure Fabrication Using IR-FELs and its Optical Properties, 1998, Nuclear Instruments and Methods in Physics Research B 144, 152-159.*

(Continued)

*Primary Examiner*—Terrel Morris
*Assistant Examiner*—Matthew D. Matzek
(74) *Attorney, Agent, or Firm*—Nixon & Vanderhye P.C.

(57) ABSTRACT

A fibre or fabric comprising silicon for use as a medical fibre or fabric. The silicon present can be biocompatible, bioactive or resorbable material and may also be able to act as an electrical conductor. In addition, porous silicon may be used as a slow release means for example for drugs or fragrances, or as a collector for example for sweat. Novel fibres, fabrics and methods of preparation of these are also described and claimed.

12 Claims, 15 Drawing Sheets

FOREIGN PATENT DOCUMENTS

| | | |
|---|---|---|
| GB | 2 363 115 A | 12/2001 |
| JP | 8-164153 A | 6/1996 |
| JP | 9-296366 A | 11/1997 |
| JP | 2001-055667 A | 2/2001 |
| SU | 1326268 A | 7/1987 |
| WO | WO 00/66190 * | 11/2000 |
| WO | 02/067998 A | 9/2002 |

OTHER PUBLICATIONS

Huong et al, "A Raman spectroscopic study of photoluminescent porous silicon fibres", International Journal of Inorganic Materials I, 1999, 209-212.*

Wallenberger, Frederick T., "Inorganic Fibres and Microfabricated Parts by Laser Assisted Chemical Vapour Deposition (LCVD): Structures and Properties", Ceramics International, 23, 1997, 119-126.*

Canham et al; "Will a Chip Every Day Keep the Doctor Away? Si Imiplants"; Physics World, Jul. 2001, IOP Publishing, UK, vol. 14, No. 7, pp. 27-32, XP008010482.

Hetke et al; "Silicon Ribbon Cables for Chronically Implantable Microelectrode Arrays"; IEEE Transactions on Biomedical Engineering, Apr. 1994, USA, vol. 41, No. 4, pp. 314-321, XP002238344.

Patent Abstract of Japan, vol. 1998, No. 03, Feb. 27, 1998 & JP 09 296366 A, Nov. 18, 1997.

* cited by examiner

MEDICAL FIBRES AND FABRICS

This application is the U.S. national phase of international application PCT/GB02/05853 filed 20 Dec. 2002, which designated the U.S. PCT/GB02/05853 claims priority to GB Application No. 0130608.3 filed 21 Dec. 2001. The entire contents of these applications are incorporated herein by reference.

The present invention relates to fibres and fabrics containing silicon for use as medical fibres and fabrics, as well as to novel fibres and fabrics suitable for these applications and others, and to methods for their production.

The production of fibres and fabrics is an ancient art. Fibres suitable for textile use possess adequate length, fineness, strength and flexibility for yarn formation and fabric construction. The first fibres available for textile use were obtained from animal and plant sources. Cotton, wool, jute, silk and flax are today the most common natural fibres. Nylon, rayon and polyester are common synthetic fibres.

It is now possible to manipulate ultrafine fibres into fabrics, for example using techniques used to produce woven metallic jewellery and Denier-grade stockings. Nylon fibres created by spinnerets for example have diameters of about 25 microns.

The use of fabrics and other fibrous forms as biomaterials dates back to the early Egyptians and Indians. Linen strips and sutures were used with natural adhesives by the Egyptians to draw the edges of wounds together. The American Indians used horsehair, cotton and thin leather strips for similar purposes. Use of fabrics as biomaterials was initially viewed as a new application of conventionally woven and knitted textiles. Over the past few decades the development of sophisticated polymer and fibre processing technologies, nontraditional fabric forms and fibrous products have also been employed.

These products may have a variety of medical applications, depending upon their precise nature and form. For example, fibres and fabrics may have general surgical applications, for examples as sutures, threads or meshes. In the cardiovascular fields, they may be incorporated for example in artificial heart valves. Orthopaedic prostheses such as tendons and ligaments utilise products in the form of fibres and fabrics and they may also have percutaneous/cutaneous applications such as in shunts and artificial skin.

The particular materials currently used in medical textiles include modified natural polymers, synthetic nonabsorbable polymers and synthetic absorbable polymers.

However, most commercial polymer textile fibres have various additives (such as dyes, antistatic agents, delustrants, photostabilisers) which may reduce their biocompatibility and thus limit the options for using these in medical applications. Although some may be biodegradable, it is difficult to ensure that fibres do not lose their mechanical strength at too early a stage in the tissue replacement process.

The applicants have developed new medical fibres and textiles.

According to the present invention there is provided a fibre or fabric comprising silicon for use as a medical fibre or fabric.

As used herein, the term "silicon" refers to elemental silicon material which is a semiconductor. For the avoidance of doubt, it does not include silicon-containing chemical compounds such as silica, silicates or silicones, although it may include composites of semiconducting silicon combined with medical-grade polymer, ceramic or metal phases. It may also include doped semiconducting silicon where concentrations up to the atomic percent level of elements like boron or phosphorus are incorporated into the silicon lattice to raise electrical conductivity. Porous silicon may be referred to as "pSi", crystalline silicon as "c-Si" and amorphous silicon as "a-Si".

Silicon has several particular advantages for use in this way. In particular, fibres and fabrics can be produced with a wide range of desirable properties, including biocompatability, resorbability or biodegradability or bioactive properties.

Furthermore, such fibres or fabrics may have semiconducting properties, which may be particularly useful in the context of certain applications, for example, in implants, protheses and the like, where controlled levels of electric current may be applied to stimulate incorporation into the body.

As used herein, the term "fibre" refers to a unit of matter having length at least 100 times their diameter or width.

The term "fabric" may be defined as thin, flexible and porous materials made by any combination of cloth, fibre or polymer. Cloth is a thin flexible material made from yarn, and yarn comprises a continuous strand of fibres.

The expression "bioactive" refers to materials, which when used in vivo, elicit a specific biological response that results in the formation of a bond between living tissue and that material.

"Biocompatible" as used herein refers to materials which, in thin film form, are acceptable for use in at least some biological applications.

As used herein, the term "resorbable" relates to material which will dissolve at normal physiological temperatures (37° C.±1° C.) in simulated body fluid, over a period of time, for example of up to 8 weeks, and generally at less than 2 weeks. Simulated body fluid in this case may comprises a solution of reagent grade salts in deionised water so that the ionic concentration reflect that found in human plasma, as shown in the following Table 1, or alternatively it may comprise a simulated synovial fluid, sweat, urine, or other body fluids. In simulated human plasma, the mixture is buffered to physiological pH values (7.3±0.05), preferably organically, using for example trihydroxymethylaminomethane and hydrochloric acid.

TABLE 1

| Ion | Concentration (mM) | |
|---|---|---|
| | Stimulated Body Fluid | Human Plasma |
| $Na^+$ | 142.0 | 142.0 |
| $K^+$ | 5.0 | 5.0 |
| $Mg^{2+}$ | 1.5 | 1.5 |
| $Ca^{2+}$ | 2.5 | 2.5 |
| $HCO_3^-$ | 4.2 | 27.0 |
| $HPO_4^{2-}$ | 1.0 | 1.0 |
| $Cr^-$ | 147.8 | 103.0 |
| $SO_4^{2-}$ | 0.5 | 0.5 |

WO 97/06101 describes the formation of silicon in a form in which is it biocompatibile, bioactive and/or resorbable. In a particularly preferred embodiment, the silicon used in the invention is porous silicon. Porous silicon may be classified depending upon the nature of the porosity. Microporous silicon contains pores having a diameter less than 20 Å, mesoporous silicon contains pores having a diameter in the range of 20 Å to 500 Å; and macroporous silicon contains pores having a diameter greater than 500 Å. The nature of the porosity of the microparticles or fibres of silicon used in the invention may vary depending upon the intended use.

Factors such as the need for biocompatability, resorbability and bioactivity need to be balanced against the need for mechanical strength and other physical factors discussed more fully below.

In particular the silicon used in fibres and fabrics for use as medical fibres and fabrics is mesoporous silicon, which is resorbable.

The silicon fibre or fabric which is the subject of the invention may take various forms, some of which are novel and these form further aspects of the invention.

In one embodiment, silicon containing fibres for use in the invention are prepared by incorporating silicon microparticles, and preferably porous silicon microparticles, to a preformed fabric. This may comprise any of the known fabrics, but in particular is a biocompatible fabric such as cotton, linen or a biocompatible synthetic fabric.

Preferably the silicon microparticles are bound to the surface of the fabric by covalent bonds. This can be achieved in various ways. For example, hydroxy groups may be formed on the surface of the silicon, for example by treatment with ozone in the presence of U.V. light. These may then be reacted with surface groups on the fabric directly, or more preferably, they may first be functionalised with a reactive group. Examples of such functionalisation reactions are described in WO 00/66190 and WO 00/26019.

In particular the microparticles are bound by reaction with a compound of formula (I)

X-R-Y    (I)

where Y is a leaving group such as trimethoxysilane, R is a linking group, such as $C_{1-6}$alkylene and in particular $C_{2-4}$alkylene such as propylene, and X is a reactive functionality, such as halo and in particular chloro. The reaction is suitably effected by appropriate input of thermal energy or light.

This reaction converts the surface hydroxy groups to groups of formula —O—R—X, where X and R are as defined above. Subsequent reaction with for example surface hydroxy groups on the fabric, will result in the silicon microparticle becoming covalently bound to the surface by an alkylether link. The subsequent reaction is suitably effected in an organic solvent such as toluene or an alcohol such as $C_{1-4}$alkyl alcohols, at elevated temperatures, for example at the reflux temperature of the solvent.

Thus a further aspect of the invention comprises a fabric having silicon microparticles incorporated therein. In particular, the silicon microparticles are covalently bound to the fabric.

The inclusion of silicon microparticles, and particularly porous microparticles, will enhance the bioactivity of the fabric. Furthermore, silicon particles may be added at a sufficient density to bring about particle-to-particle contact which is able to provide an electrically continuous pathway. In this way, the fabric may acquire semi-conducting properties which may be of use in the medical application to which it is put.

Suitable fabrics include biomedical fabrics such as cotton, linen or synthetic polymers, which may be absorbable or non-absorbable.

In an alternative embodiment, silicon is incorporated into a fibre, which may then be processed into fabrics, either alone or in combination with other types of fibre.

The silicon fibres used may comprise silicon alone, or they may be in the form of a composite of silicon with other materials.

The preparation of some silicon and silicon composite fibres is known. For example, Japanese patent no. JP9296366A2 describes the preparation of composite fibres, fabricated by either vapour deposition of thin Si/SiOx films onto polyester fibres or spinning of a polyester/silicon mixture.

Pure Silicon fibres of varying crystalline perfection have also been realised by a number of techniques:

Single crystal silicon fibres and their preparation are described for example by B. M. Epelbaum et al. in Cryst. Res. Technol. 31, p1077-1084 (1996). In this method a crucible containing molten Si is connected to a graphite nozzle that acts as the shape defining die. Due to molten silicon having a low viscosity, high surface tension and high chemical reactivity, pulling of single crystal fibres is difficult. Three types of crucible die arrangement were designed and tested. Single crystal fibres of diameter in the range 100-150 microns and lengths up to 80 mm were grown successfully. The maximum pulling speed achieved was 1 mm/minute.

Laser-assisted chemical vapour deposition (LCVD) has been shown to provide a higher growth rate synthesis route for a wide variety of inorganic fibres, including silicon. In the LCVD technique a laser beam is focussed onto a point inside a reactor to initiate chemical vapour deposition in the direction of the laser. By moving the substrate at the same speed as the deposition rate, a continuous fibre is realised. For example, with the methods described by P. C. Nordine et al in Appl. Phys. A57, p97-100 (1993), silicon fibre growth rates up to 30 mm/minute were achieved using silane gas pressure of 3.4 bar and Nd: YAG laser power up to 200 mW. At fibre tip temperature of 525-1412 C, poly-Si fibres of 26-93 micron diameter were realised with varying degrees of crystallinity.

Silicon fibres have also been realised by the VLS method, as disclosed in the early paper of R. S. Wagner and W. C. Ellis in Appl. Phys. Lett. 4, p89-90 (1964). Here the V represents a vapour feed gas or gas mixture, the L represents a liquid catalyst and the S represents a solid fibre product. In this method it is the size of the metal catalyst droplets that primarily determine the resulting fibre diameter. The synthesis of both crystalline silicon microfibres and more recently, nanowires, has been demonstrated using, for example, gold as the catalyst and silane as the vapour phase reactant. There are also many related early reports of silicon "whiskers", "needles" and "filaments" of relatively short length (under 10 cms) as reviewed in Whisker Technology (John Wiley & Sons 1970), Edited by A. P. Levitt.

The VLS method should be adaptable to mass production of short silicon fibres for air laying or wet laying. Incorporation of silicon onto/into pre-existing fibres/yarns should be most suitable for weaving, knitting and embroidery of structures of many metres length.

Silicon microwires and the preparation are described for example by J. J. Petrovic et al. J. Mater. Res. October Issue 2001. In this method, an optical FZ Si growth system was adapted to generate microwires by the "Taylor microwire technique". The material to be processed is melted within a glass tube and the softened glass with the molten material mechanically drawn out into a fine wire in a similar manner to that of drawing of optical glass fibres. The working temperature of the glass needs to exceed the 1410° C. melting point of silicon, where the method was applied to pure silicon. In this study Vycor glass (Corning 7913) was used which has a softening temperature of 1530° C. and a working temperature of 1900° C. A pure Si charge was loaded into evacuated tubes that were then heated to 1900°

C. using halogen lamps and mechanically pulled. Flexible 10-25 micron diameter poly-Si microwires were synthesised by this method in continuous lengths up to 46 cms.

J. F. Hetke et al. IEEE Trans. Biomed. Engn.41, 314-321 (1994) describes the design, fabrication and testing of "ultraflexible" ribbon cables for use with CNS microprobes. Standard Si wafers were subjected to photolithography, deep boron doping and multidielectric deposition to define the cables that were subsequently floated off by using a boron etch-stop and a fast wet etch to dissolve the underlying wafer. Cables as thin as 2-3 micron and as thick as 20 micron were realised by varying the boron diffusion temperature and time.

Multistrand cables containing 20-30 micron strands are also described here, and these provided "enhanced flexibility in the radial and lateral directions". An image of a 5 strand ribbon cable tied into a knot was shown to illustrate flexibility. Such designs had lengths of 1-5 cms and total widths ranging from 60-250 micron. Fibres produced in this way have good flexibility as illustrated in J. F. Hetke et al., Sensors and Actuators A21-23,999-1002 (1990), where a single 15 micron thick strand is shown bent through 180 degrees.

Although there are such examples of silicon fibres, fibre arrays of a form and structure suitable for medical fabric construction are novel, and as such form a further aspect of the invention.

The applicants have found that fibres may also be produced by cutting a silicon wafer using a saw with a sufficiently small blade and pitch, for example a 75-micron blade and a 225-micron pitch. Preferably, multiple parallel cuts are formed in a single wafer to form a comb like structure, which allows for the production of multiple fibres. In a particularly preferred embodiment, two such comb-like structures are produced, and then interweaved in a perpendicular manner. In this way, the fibres of one comb forms a waft and the fibres of the other wafer form a weft of a fabric like structure. Cut fibres may be subject to cleaning for example, ultrasonic cleaning, and/or etching, for example by anisotropic wet etch to remove saw damage and/or to shape the cross section of the fibres.

Other methods for producing silcon or silicon composite fibres may be used however. For example, hollow amorphous silicon microfibres may be obtained by coating a fibre, such as a polymer, metal, ceramic (including glass) fibre, preferably with a hollow core, with silicon and particularly amorphous or polysilicon. This may be achieved for example by sputtering or continuous vapour deposition (CVD). Subsequently the initial fibre can be dissolved, leaving a hollow amorphous or polysilicon microfibre. This may then be porosified if desired. If the initial fibre is a biocompatible material, for example a biodegradable suture, dissolution may not be necessary or desirable.

In an alternative embodiment, silicon fibres are formed by threading together silicon beads to form flexible chains on a resilient thread or wire, which is preferably a biocompatible or biodegradable suture. The resultant structure, which is novel and forms a further aspect of the invention, is therefore similar in structure to strings of beads found in jewellery. Individual silicon beads may be of various sizes, depending upon the intended nature of the fibre, or the fabric produced therefrom.

For example, beads may be on a macroscale, for example of from 0.5 to 5 mm in diameter. In these cases, they may be formed by drilling holes through appropriately sized silicon granules and subsequently threading through the resilient thread or wire.

Where microscale beads are required, for example of from 10 microns-500 microns diameter, they are suitably prepared by photolithography and surface micromachining. For example, a silicon membrane may be supported on a dissolvable surface, such as a silicon oxide surface. Trenches for example of up to 500 microns and preferably about 50 microns in depth can then be etched into the upper surface of the membrane for example by a dry etching or photolithographic process. A further silicon membrane may then be deposited over the surface, so that the trench forms a central cavity. This structure can then be etched photolithographically to the desired depth, representing the diameter of the desired bead, to form substantially parallel trenches on either side of the central cavity. Further channels may be etched which channels are substantially perpendicular to the trench to trace out the desired bead shape. Once this has been done, and a suitable thread or suture passed through the central cavity, the dissolvable surface may be removed.

These production methods form yet further aspects of the invention.

Fibres and composite fibres obtained using any of the above methods may be suitable for use in the invention. Preferably however, the fibres used are porous, or contain porous silicon beads and these can be obtained by porosifying the fibres or strings of beads produced as described above, using for example, methods described in U.S. Pat. No. 5,348,618 and Properties of Porous silicon (IEE 1997 Ed by L. T. Canham).

In a particular embodiment therefore, the invention provides a method of preparing a porous silicon fibre, which method comprises forming a silicon fibre, in particular by one of the melt pulling, Laser-assisted chemical vapour deposition (LCVD), VLS methods, coating of sacrificial fibrous material or micromachining methods described above, and thereafter porosifying the silicon, for example by anodisation or stain etching.

The applicants have found that porous silicon fibres may be produced directly by cleaving mesoporous films on silcon wafers. The films may be formed using conventional methods, for example by anodisation of a silicon wafer in hydrofluoric acid (HF) for example 40 wt % HF, and ethanol, suitably in equal volumes. Fibres may be cleaved mechanically, for example by breaking them over a solid edge, for example of a glass surface, for instance a glass slide, which may be covered in filter paper. The wafer may be prescored or scribed before the breaking is carried out.

Porous or partially porous silicon containing fibres and fabrics are novel and as such form a further aspect of the invention.

Substantially pure silicon fibres, for example of length greater than 100 cm, are also novel, and these also form an aspect of the invention. Preferably, these are porosified as discussed above.

As used herein the expression "substantially pure" means that the silicon is at least 98% pure, more suitably at least 99% pure, and preferably 100% pure.

For the purposes of the invention, fibres consisting of or comprising silicon can be used directly as sutures, if they have sufficient flexibility and strength. The factors required to achieve fibres having high levels of flexibility are discussed further below.

Alternatively, they may be converted into fabrics or yarns using one or more of any of the major processes common in textile manufacture. These include spinning, embroidery, weaving, knitting, braiding, fibre bonding, air-laying, wet laying, and laminating. The possibility of applying all these various techniques in the production of fabrics for medical use provides the opportunity to achieve complex 2-dimensional and 3-dimensional topographies. This may be particularly useful in certain applications, for example when the fabric is used to assist in-bone growth, open meshes would be preferred.

Silicon is a tough but brittle material and porous silicon is prone to cracking. It is hence surprising that porous fibres can be produced which are strong and flexible enough to be weaved into intricate patterns.

Most natural fibres such as wool, cotton and flax are not long enough to be processed into cloth without further treatment. They are converted to usable thread by a process known as spinning, where fibres are first laid out parallel to one another ("carded") and twisted together into a "yarn" (as illustrated for example in FIG. 2 hereinafter). Such processes may also be applied to fibres comprising silicon.

Substantially pure silicon yarn is also novel, and forms yet a further aspect of the invention.

Embroidery involves the formation of stitches on a base cloth, which means that there is a high flexibility in design. The base cloth may then be dissolved away after the stitching process is terminated. This process may be particularly good for mimicking natural fibrous arrays such as ligaments. There is also potential in fracture fixation where load bearing threads are arranged optimally with an open mesh for tissue in-growth.

The weaving process requires the interlacing of two separate sets of elements to produce a fabric. The element called "warp" is set down first, usually in a parallel arrangement; the second element called the "weft" then interlocks with the warp to create the stable planar structure. Weaving does not require too much fibre flexibility. In a simple mechanical loom, the warp threads run off a roller as wide as the finished bolt of cloth will be. The threads run through a set of wires running vertically which can be moved up and down. Each wire has a small eye or ring, in the middle through which the warp yarn runs. By simple mechanical arrangements it is possible to raise every alternate ring, making a space for which the weft can pass. The weft is carried by a "shuttle" or jets of air/water. When the weft has passed through the warp it is pushed down tightly against the previous thread with a comb-like frame. The rings carrying the warp threads are now depressed, the shuttle turned around and the second "pass" between a set of threads is made. The fastest industrial looms operate at around 200 passes a minute.

Woven fabrics usually display low elongation but high breaking strength. They may have a variety of 2D and 3D topography, depending upon the type of weave used, and typical examples are illustrated in FIG. 1 herein after. If required, the 3D topography of a particular fabric can be modified by for example localised melting of the fibres during fabrication assembly. The silicon fibre network in a composite fabric is electrically conductive and can thereby be used to selectively heat up intersecting polymer fibres to form a more rigid mated lattice.

Knitting is a continuous single element technique illustrated for example in FIG. 3 hereinafter, in which a series of loops are interlocked vertically through the repetition of knitting stitches retained on some kind of tool or frame. The tensile strength of knitted fabrics is usually inferior to that from weaving but their flexibility and stretchability is greater.

Braiding is a process that utilises simple interlacing of a single set of elements with out any type of link, loop, warp or knot. It is differentiated from weaving by the warp serving as the weft, and by interlacing being in a diagonal or generally oblique pattern. Braiding is frequently called plaiting, webbing or interlacing.

Fibre bonding is a technique commonly used in the production of large-volume health products where fibre-to-fibre mating is generated by heat or solvents.

Air-laying and wet-laying are techniques suitable for forming fabrics from very short fibres. In air laying, the fibres are fed into an air stream before being deposited on a moving belt or perforated drum to form a soft web structure of randomly oriented fibres. Similarly wet-laying uses a mixture of fibres and water, which is deposited on a moving screen before being drained to form a web, consolidated between rollers and allowed to dry.

Finally, laminating is a way of joining of one fabric to another using an adhesive.

Alternatively, silicon and particularly amorphous or polysilicon may be coated onto a pre-existing fabric, for example by sputtering or continuous vapour deposition (CVD). Suitable fabrics may comprise any of the known fabrics, but in particular is a biocompatible fabric such as cotton, linen or a biocompatible synthetic fabric such as polyester gauze as described above. Once coated in this way, the resultant silicon coating may optionally be porosified by stain etching as is known in the art, and described above.

Any or all of these techniques can be applied in the production of fabrics used in the present invention. Their applicability in any particular case depends upon the nature of the silicon fibres being used, and the requisite properties of the final fibre or fabric product.

Factors which need to be taken into account when selecting the type of fibre required in any particular case, and the technique used to convert this to a fabric include stress, strain, tensile fracture strength, malleability, and work of fracture.

Stress is simply load per unit area (units of N/m2 or Pa). Strain is simply the amount of stretch under load per unit length (a ratio). Different materials are stretched/compressed by enormously varying degrees by extending/compressive forces. The corresponding ratio stress/strain, the Young's modulus (units of N/m2 or Pa) thus describes the "stiffness" or elastic flexibility. It varies from 7 Pa for rubber, 1.4 kPa for most plastics, 2 MPa for steel to about 1.2 GPa for diamond.

Tensile fracture strength is the stress needed to break/fracture a material (N/m2 or Pa) by stretching it. It also varies considerably about 4 MPa for ordinary concrete, 50 MPa for plastics to 2 GPa for steel. Some values for materials used in fabrics are 40 MPa (leather), 350 MPa (cotton and silk). For brittle materials, fracture strength, FS, is controlled by critical flaws and given by the Griffith equation;

$$FS=(2VE/c)^{0.5}$$

Where E is the Young's modulus, 2V is the fracture energy required to form two new surfaces and c is the critical flaw size.

Malleability refers to the extent to which a metal can be manipulated before it breaks.

Work of fracture is the total energy needed to generate a fracture structure (J/m^2). For ductile materials like copper and aluminium, values range between $10^4$ and $10^6$ J/m^2, much higher than the free surface energy.

The introduction of porosity makes a material more flexible (lowered Young's modulus) but also makes it weaker (lowered fracture strength). For brittle materials strength is limited by critical surface flaws which initiate crack propagation and fracture. Although textile materials generally comprise non-porous fibres, there are examples of fabrics that contain nanometre size pores. One such material is HPZ ceramic fibre where porosity is 20%, average pore width is 1.4 nm. Single crystal "bulk" silicon has a Young's modulus of 162 GPa and a fracture strength of 7 GPa. The introduction of mesoporosity in p+ silicon has been shown to significantly decrease Young's modulus according to the equation;

$$E=(120 \times p^2)\text{GPa}$$

where p is the relative density in the range 0.1 to 0.7, corresponding to 90 to 30% porosity. Values as low as 1 GPa can be achieved in high porosity material.

Micromachined silicon structures will generally have the mechanical properties of bulk silicon prior to their porosification. However, silicon fibres, like glass fibres, get significantly stronger when the diameter drops below 5 micron.

For glass the important defect is usually the surface crack. In a brittle crystal like silicon however, surface steps can act as initiators of crack propagation by locally increasing stress. Thus it may be preferable to reinforce the surface of the silicon fibres used in the invention, for example by resin bonding.

Polycrystalline silicon may be used in the invention, and therefore whenever the term "silicon" is used herein, it may include this form. Polycrystallinity does not lower strength provided the surface energy of the grain boundaries exceeds that of the crystal fracture planes.

Similarly amorphous silicon may be biologically acceptable or bioactive, and therefore whenever the term "silicon" is used herein, it may include this form unless specified otherwise.

To achieve sufficient flexibility for use in medical fibres and fabrics, non-porous silicon fibres are suitably less than 50 micron in diameter. Porosifying part of the fibre will improve flexibility at a given diameter but decrease strength.

A partially porous silicon fibre will not be fully biodegradable but could have substantially greater strength, and thus be preferable in certain situations.

In order to avoid the surface failure mechanisms discussed above, introducing porosity into the fibre core rather than at the surface coating would be preferable in order to improve strength. This could be realized by selective anodising of a p++/n− fibre or poly-Si coating of a wholly porous fibre or partial sintering of a wholly porous fibre.

Fabrics prepared from substantially pure silicon fibres are novel and form a further aspect of the invention.

In yet a further aspect, the invention provides a process for preparing a medical fabric, which process comprises weaving, knitting, embroidering or fibre bonding substantially pure silicon.

Fibres and fabrics constructed from silicon or silicon composites may be semi-conducting. Thus the invention further provides an electrically conductive silicon or silicon composite fibre or fabric. Such fibres and fabrics are particularly useful in medical applications since the semiconducting nature allows for good distribution of electrical charge, where these are used in therapy. A particular form of such a fabric is a silk based fabric which comprises silk warp threads and low resistivity silicon containing weft threads.

Thus in a further aspect the invention provides a method for enhancing tissue growth, which method comprises applying to a patient in need thereof, a semiconducting fabric comprising silicon, and passing controlled levels of electrical current through said fabric.

Fibres and fabrics as described above have a variety of medical applications. For example, fabrics which have large pores (>100 micron) for cellular infiltration can be used as scaffolds for tissue engineering. The use of the different fabrication techniques listed above provides for exceptional flexibility of 2D topography.

They may also be of use in orthopaedic prostheses where the mesoporosity of the fibres provides bioactivity whilst the macroporosity of the textile pattern directs and allows bone in-growth.

The electrical conductivity of the textile is also of benefit in orthopaedic applications where osteogenesis is controlled by application of distributed electrical charge. Invasive bone growth stimulators that utilise a wire mesh cathode are currently used in spinal fusion.

A stent is a mesh-like collar designed to serve as a temporary or permanent internal scaffold to maintain or increase the lumen of a vessel. Essential stent features include radial and torsional flexibility, biocompatibility, visibility by X-ray and reliable expandability. It is an example of a widely used implant that is currently engineered from malleable but non-biodegradable materials such as metals. A silicon or silicon containing fabric as described above, may form the basis of these stents. Particular preferred fabrics would comprise biodegradable forms and partially porous forms for eluting drugs locally. These forms would be possible using fully or partially porous silicon fibres as described above, in the production of the stents.

A further possible application for the fabrics described above is in flexible electrodes for neuro-interfacing. The macroporosity of the fabric enables tissue in-growth. In addition, the fibres used are preferable at least partially mesoporous, which means that they offer lower impedance. In order to ensure the very high electrical conductivity and stability which is important in such devices, in this case, it may be preferable to use fibres comprising a non-porous heavily doped silicon core, with a porous silicon layer that has been electroplated with an ultrathin conformal coating of a metal such as platinum or iridium.

The fabrics described above could also be used to produce "wrapped" in-vivo drug delivery systems. For instance, they may be used in the localised delivery to curved areas of an organ or for the encapsulation of drug-eluting cells. In these cases, biocompatibility of the composite formulation is essential.

In a variant on this application, they may be used in "wrapped" ex-vivo drug delivery systems. In this case, it may be preferable to use a fabric that is augmented with drug-eluting pSi particles that dissolve in sweat. In such cases, the core fabric need not be biodegradable and is a medical fabric only to the extent that it does not irritate the skin.

An extension of such applications may include textiles wherein the silicon within the fibres or fabrics is impregnated with drugs to treat the skin for dermatological conditions, which can be incorporated or comprised within dressings applied directly to the skin. In addition, such fibres and fabrics can be used for localised topical delivery of drugs used to treat conditions such as anti-inflammatory drugs, used to treat arthritic joints for instance.

Passive drug diffusion through the skin could be used in particular where small molecules like silicic acid are being diffused. Semiconducting fabric as described above might be used in an iontophoresis-type design for transdermal delivery of large biomolecules.

The electrically conducting properties of the fabrics described above makes them suitable for distributed networks for electrical stimulation. In these applications, a fabric is wrapped around a target area and can be used to electrically stimulate an array of sites simultaneously Non-occluding garments, or other wearable structures such as patches or bandages, for sweat diagnostics may also incorporate the fabrics described above. Here the fabric used, in particular for non-occluding garments, may be one with a relatively open lattice as this helps maintain normal hydration levels of skin and flexibility compared to the silicon chips currently used for this process. It also enables vastly increased area coverage. The widely distributed porous Si component acts as a large clean reservoir for collecting excreted biochemical markers.

A relatively cheap garment (e.g. teeshirt plus porosified metallurgical grade particulate polysilicon) may be employed as a one-shot sweat collection device for analysis after strenuous physical exercise.

Reservoir particles can be removed from the fabric of the garment or the like, after wear and sweat incorporation by extended sonication. Markers collected within the mesopores are then subjected to standard analysis techniques after solvent extraction. Biochemically stable silicon particles, which are preferably derivitised by techniques described in WO 00/006190, are suitably included in the garments.

The semiconductive nature of the fabric also facilitates enhanced sweating via electrical elevation of skin temperature. Joule heating of the silicon microfibres in particular in a bandage or patch like structure can locally raise temperature to a sufficient level to promote sweat production and collection. Again this can be recovered subsequently from reservoir particles of porous silicon. However, this may be applied more widely where localised heating of the skin is required. In that case, the silicon used may or may not be porous, provided the fabric is semiconducting in nature.

A method of collecting sweat using this technique, as well as a method of locally heating skin forms particular embodiments of the invention.

Hollow silicon containing fibres as described above, may suitably be employed to form fabrics for use in flexible immuniosolation networks. In this case, foreign cells used are housed in central channels of hollow mesoporous fibres. Suitably the fabric has a relatively open architecture, which encourages vascularisation around every fibre.

The porous nature (both macroporous and mesoporous) of the silicon containing fabrics described above may be utilised in wound repair, for example to deliver drugs such as antibiotics. Thus these fabrics may be used in absorptive dressings. Also polycrystalline silicon may be particularly useful in fabrics used to facilitate wound repair.

Yet a further specific application of the silicon containing fibres described above is in the production of X-ray opaque yarns. Silicon is relatively opaque to X-rays and therefore could be used instead of the current polymers, which must contain at least 50% by weight of barium sulphate to render them sufficiently opaque to be used as markers in surgical swabs or sponges.

Where the fibres or fabrics discussed above include porous or non-porous silicon, this opens up the possibility that they may be used for slow release of a variety of substances. As well as pharmaceuticals or drugs, they may include fragrances and the like. Particular examples of such substances are essential oils, which may be fragrant and/or may have a therapeutic effect.

Thus the present invention is particularly advantageous since is allows fibres and fabrics to be produced with the desired combined biodegradability and mechanical properties for a wide variety of application. The semiconducting nature of the silicon used allows for the possibility of distributing electrical charge in a medical context. Furthermore, in the case of the fabrics, the desirable effects of dual porosity (i.e. micro or meso porosity of the fibres themselves as produced for example by electrochemical etching, and macroporosity determined by selection of weave design) can be achieved, so that for example bioactive open meshes can be produced for bone in-growth and other complex 2D and 3D topographies achieved depending upon the intended end use.

The invention will now be particularly described by way of example, with reference to the accompanying drawings in which.

Figure 1:
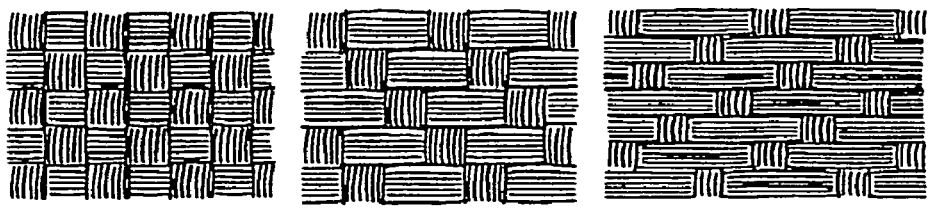
FIG. 1 illustrates diagrammatically the structure of woven fabrics.
Figure 2:
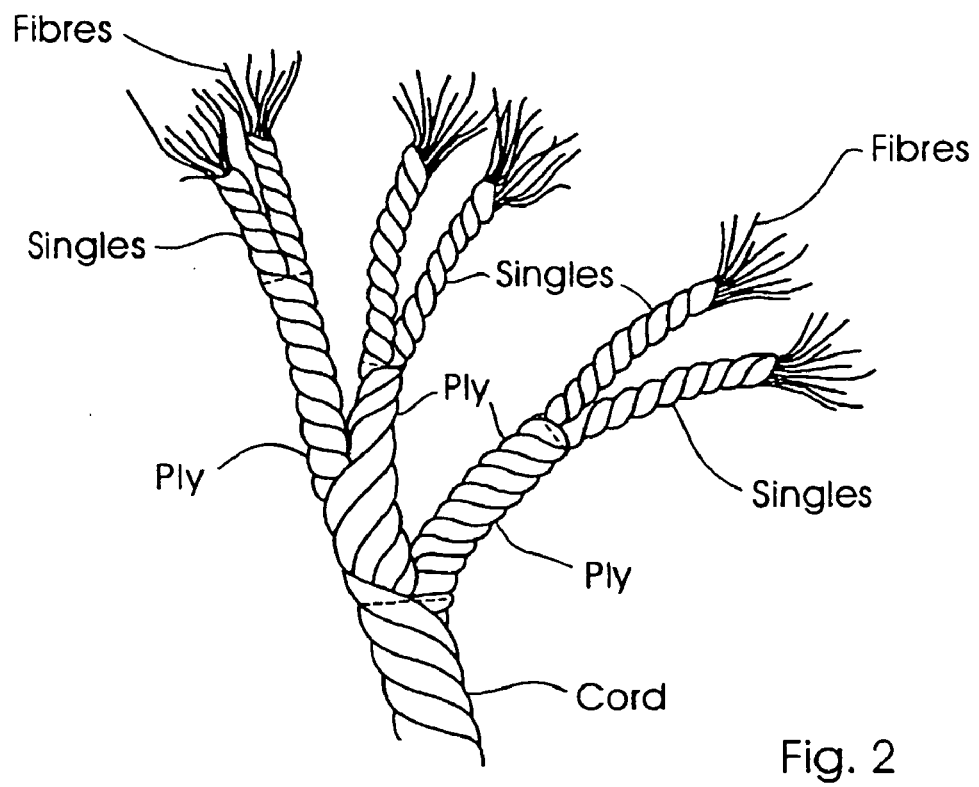
FIG. 2 illustrates diagrammatically the structure of yarns.
Figure 3A:
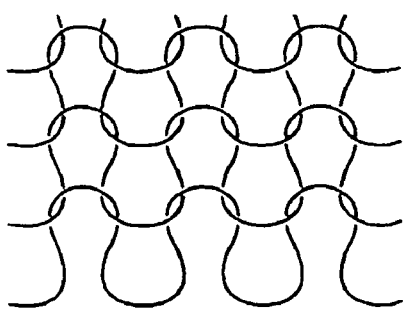
FIG. 3 illustrates diagrammatically the structure of knitted fibres.
Figure 3B:
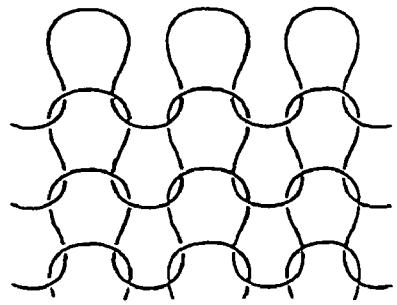
Figure 4A:
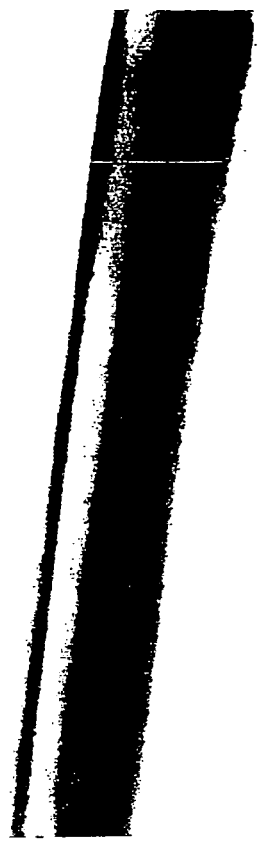
Figure 4B:
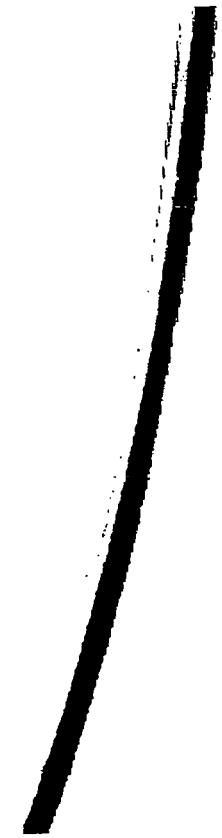
Figure 4C:
Figure 5C:
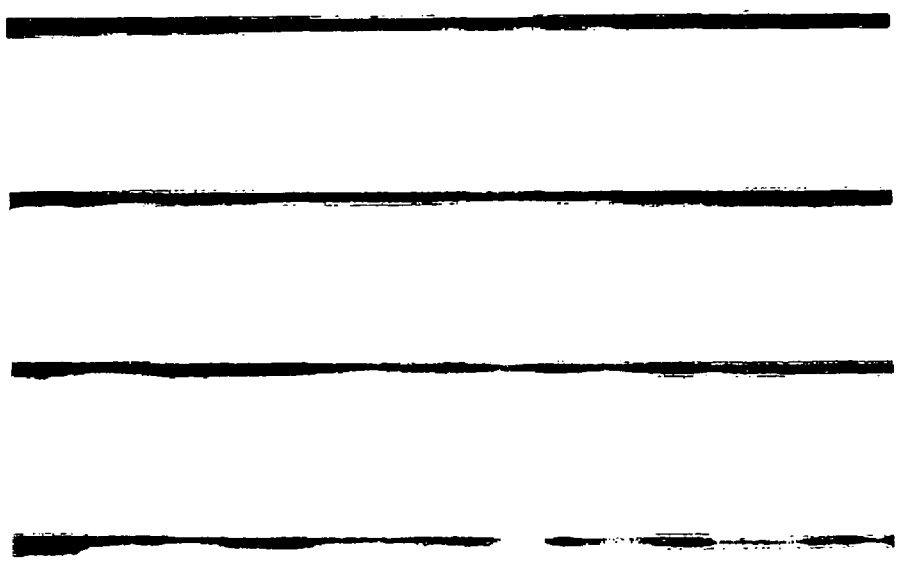
Figure 5A:
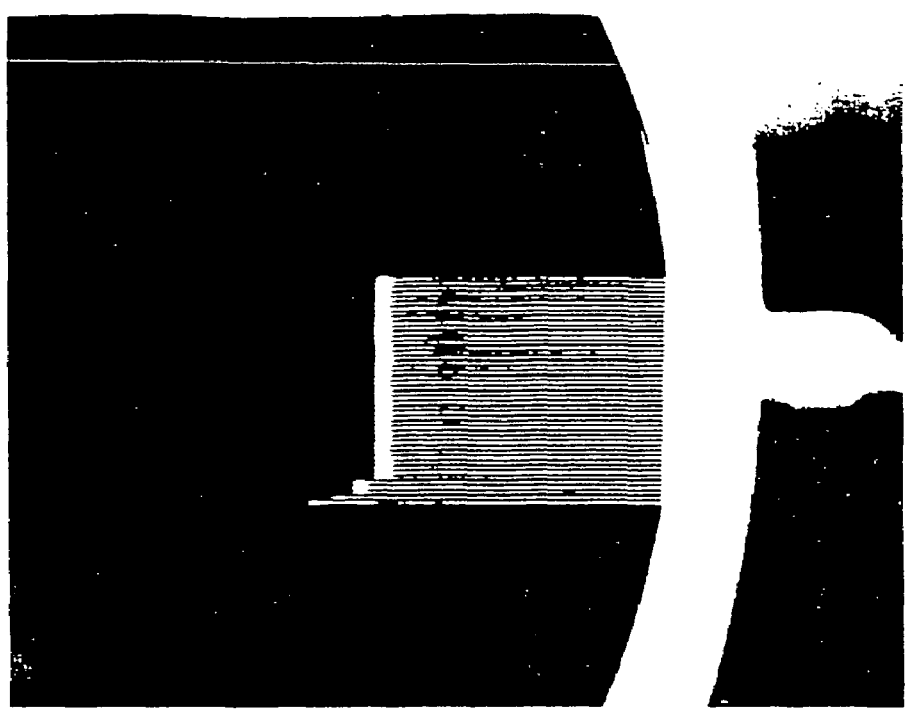
Figure 5B:
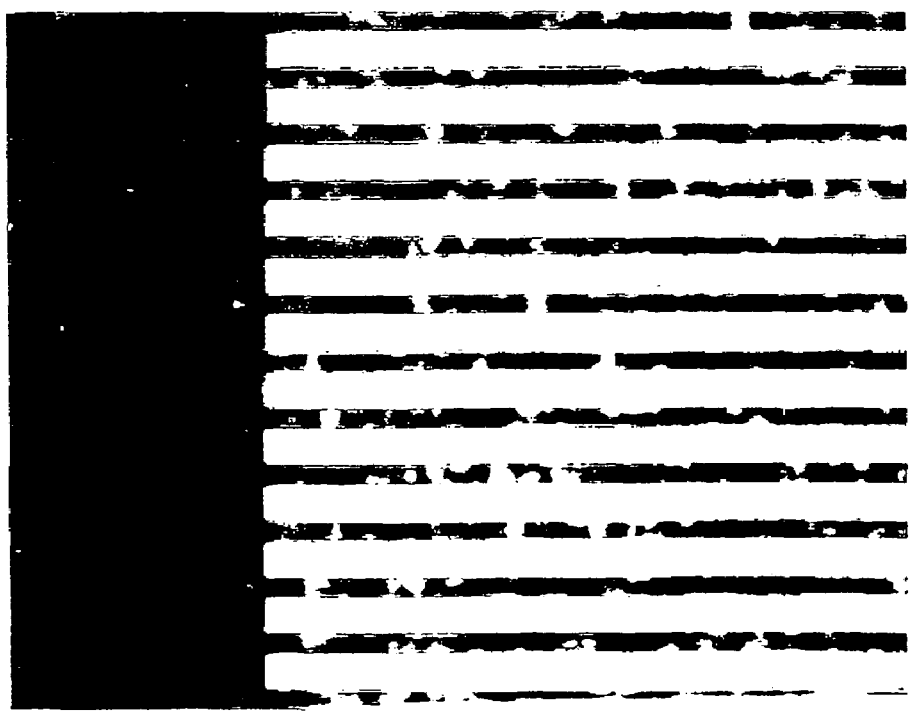
Figure 6A:
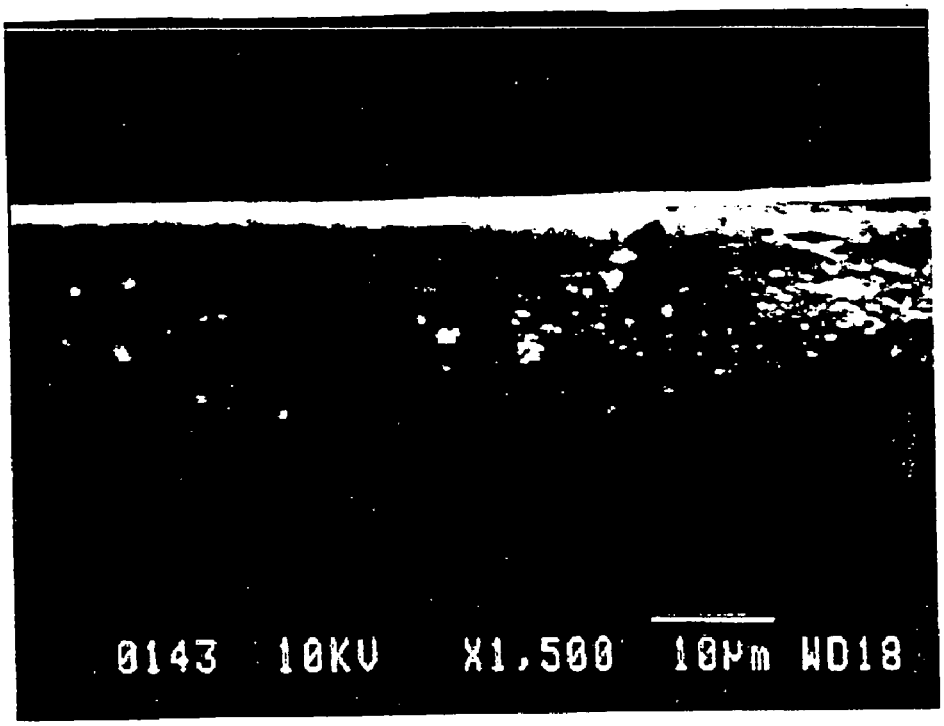
Figure 6B:
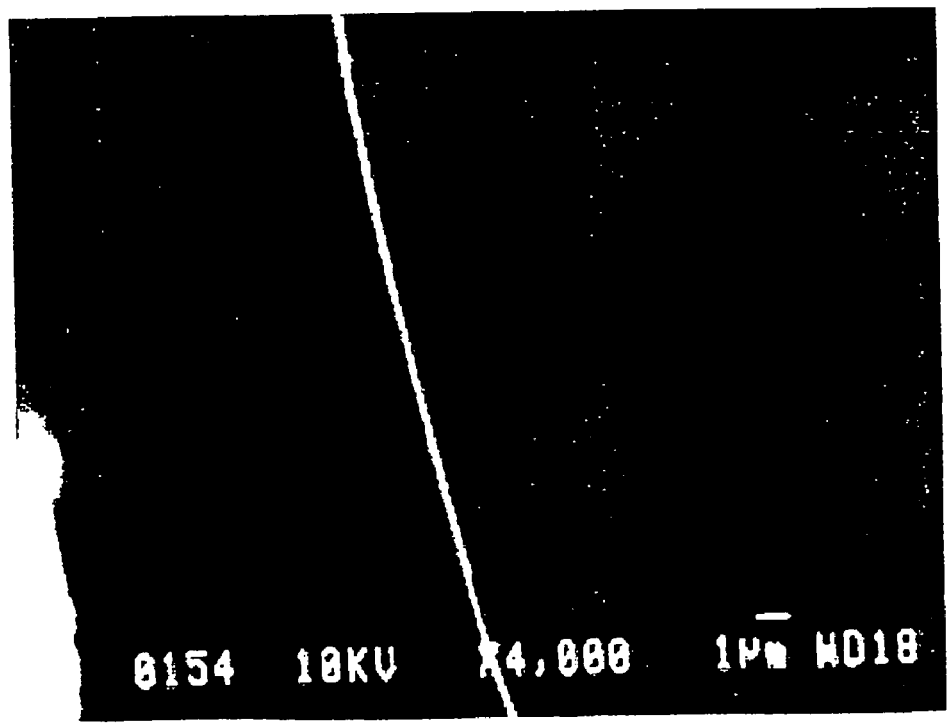
Figure 6C:
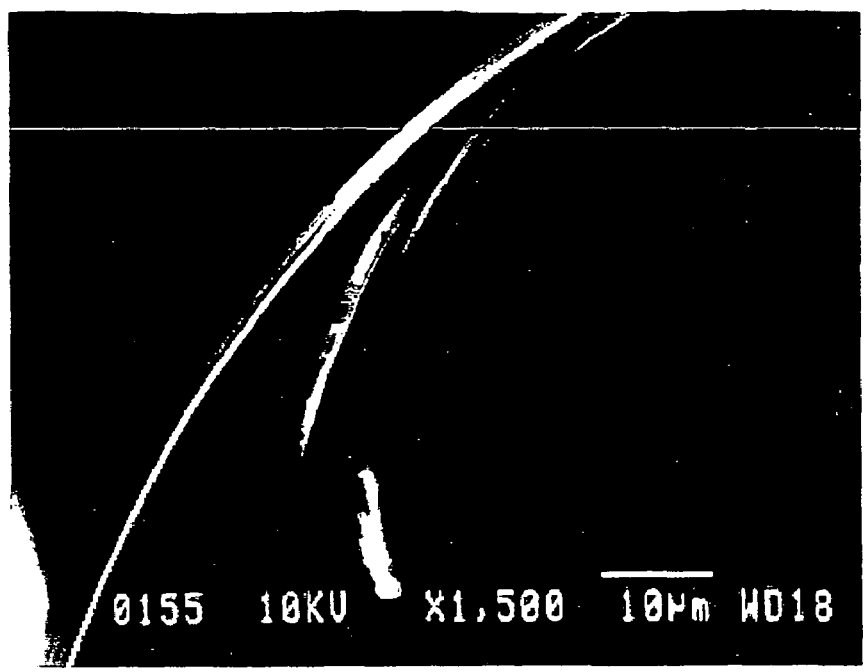
Figure 7A:
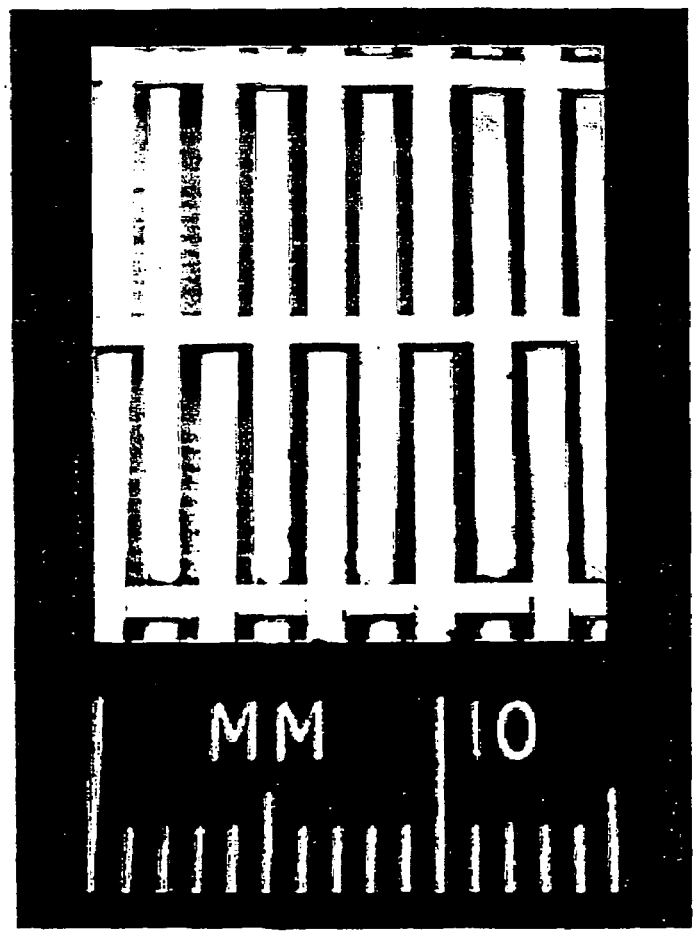
Figure 7B:
Figure 7B:
Figure 7C:
Figure 7C:
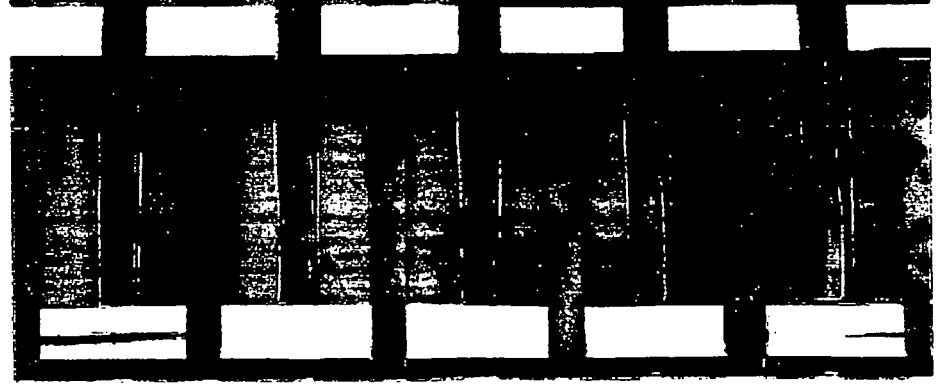
Figure 7C:
Figure 8A:
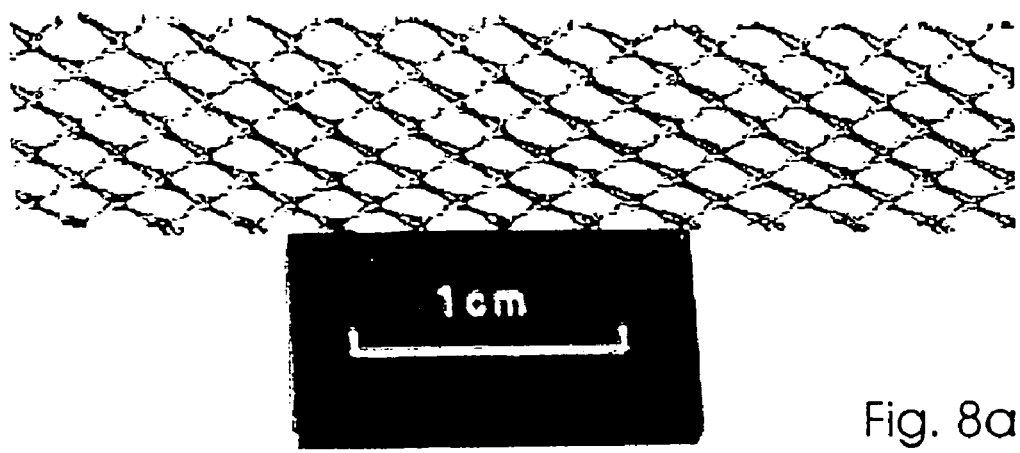
Figure 8B:
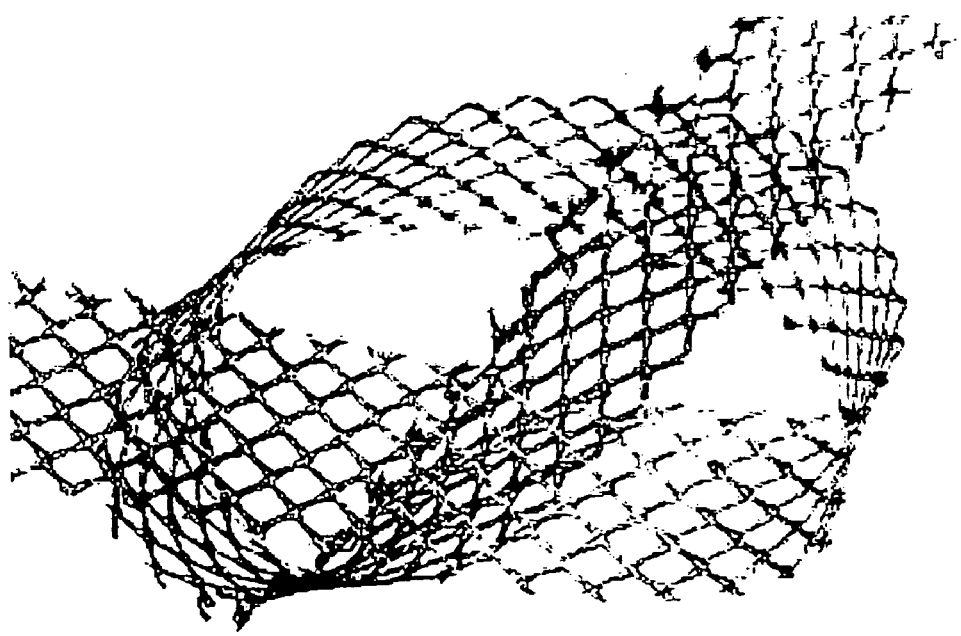
Figure 9A:
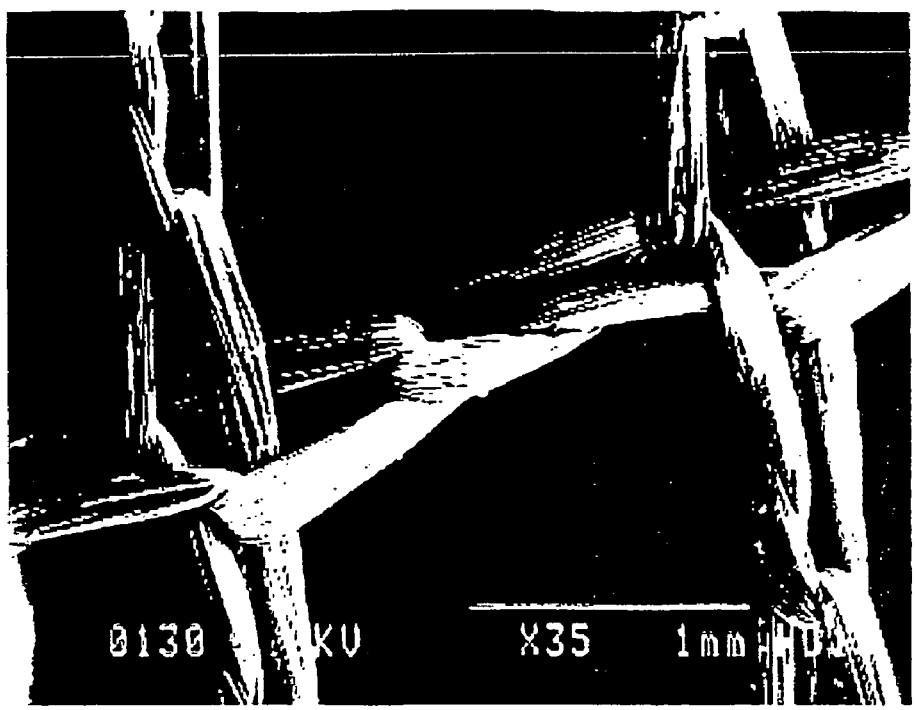
Figure 9B:
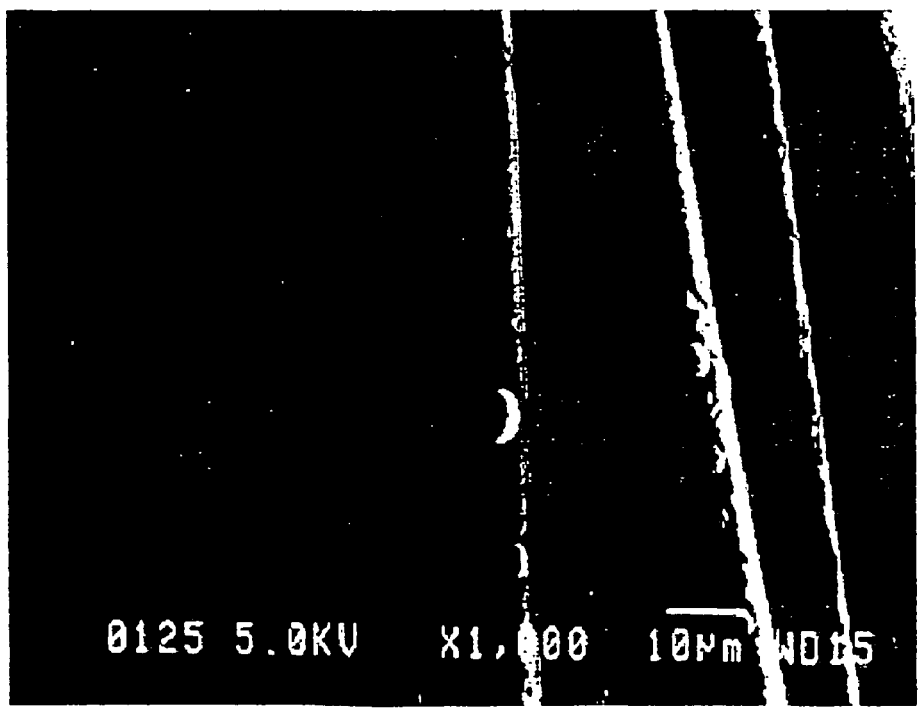

FIG. 4 shows microscope images of porous c-Si microfibres of smallest widths (a) about 100 micron (×200)(b) about 25 micron and (×200)(c) an elastically bent 100 micron wide fibre (×20), FIG. 5 shows microscope images of (a) a partially sawn wafer (×3) (b) a sawn silicon beam array (×32) and (c) an etched silicon beam array (×100), FIG. 6 shows a microscope image of a porous c-Si microfibre of smallest width (a) 20 micron (b) 4 micron, and (c) a multistrand fibre (scale and magnification shown), FIG. 7 shows microscope images of woven c-Si structures with (a) a 200 micron thick warp & weft and (b,c) 100 micron thick warp and 300 micron thick weft (scale shown), FIG. 8 shows microscope images of polyester gauze coated with 10 micron thick layer of semiconducting silicon (scale shown), FIG. 9 shows SEM images of view of the surface of the polyester gauze after coating (a,b), and the corresponding Energy Dispersive X-ray (EDX) spectrum, (scale shown)

Figure 10A:
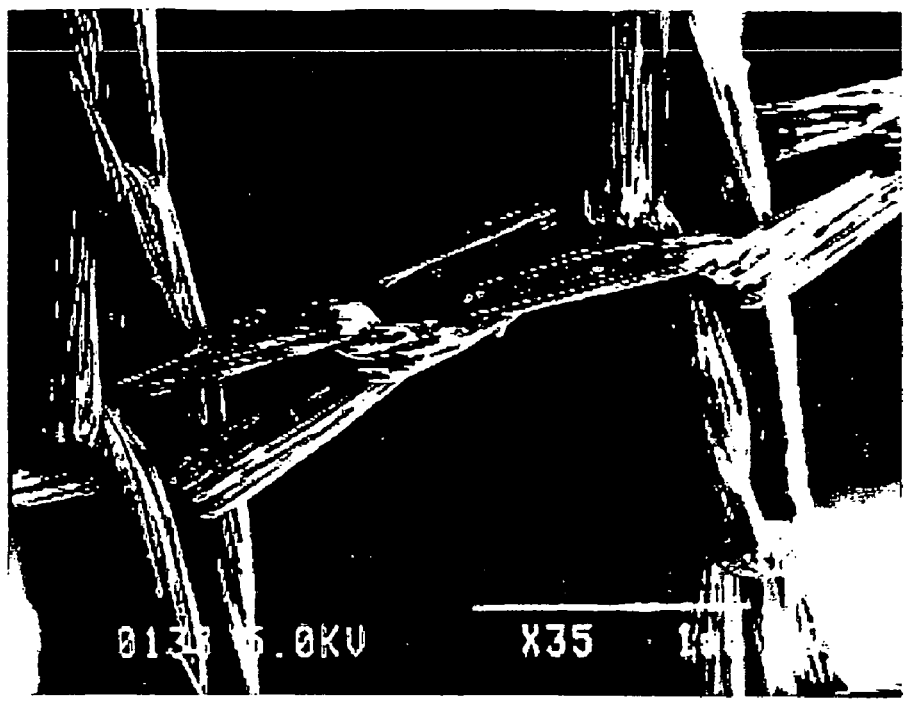
Figure 11A:
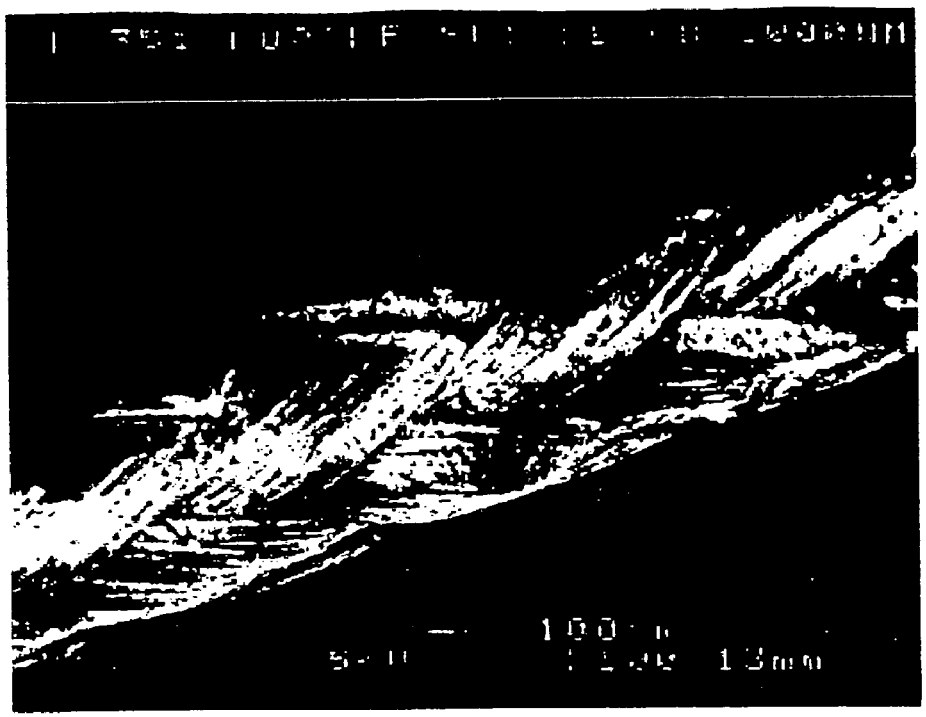
Figure 11C:
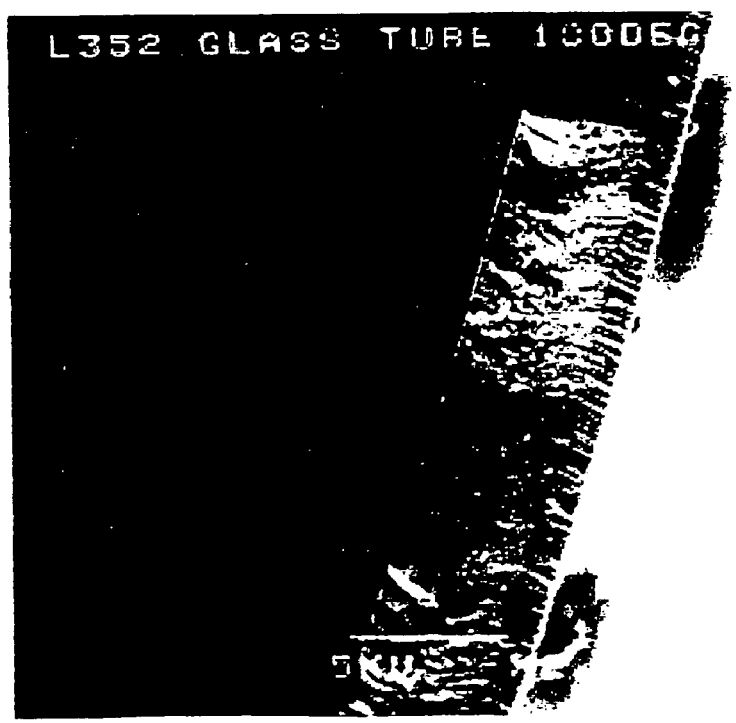
Figure 11B:
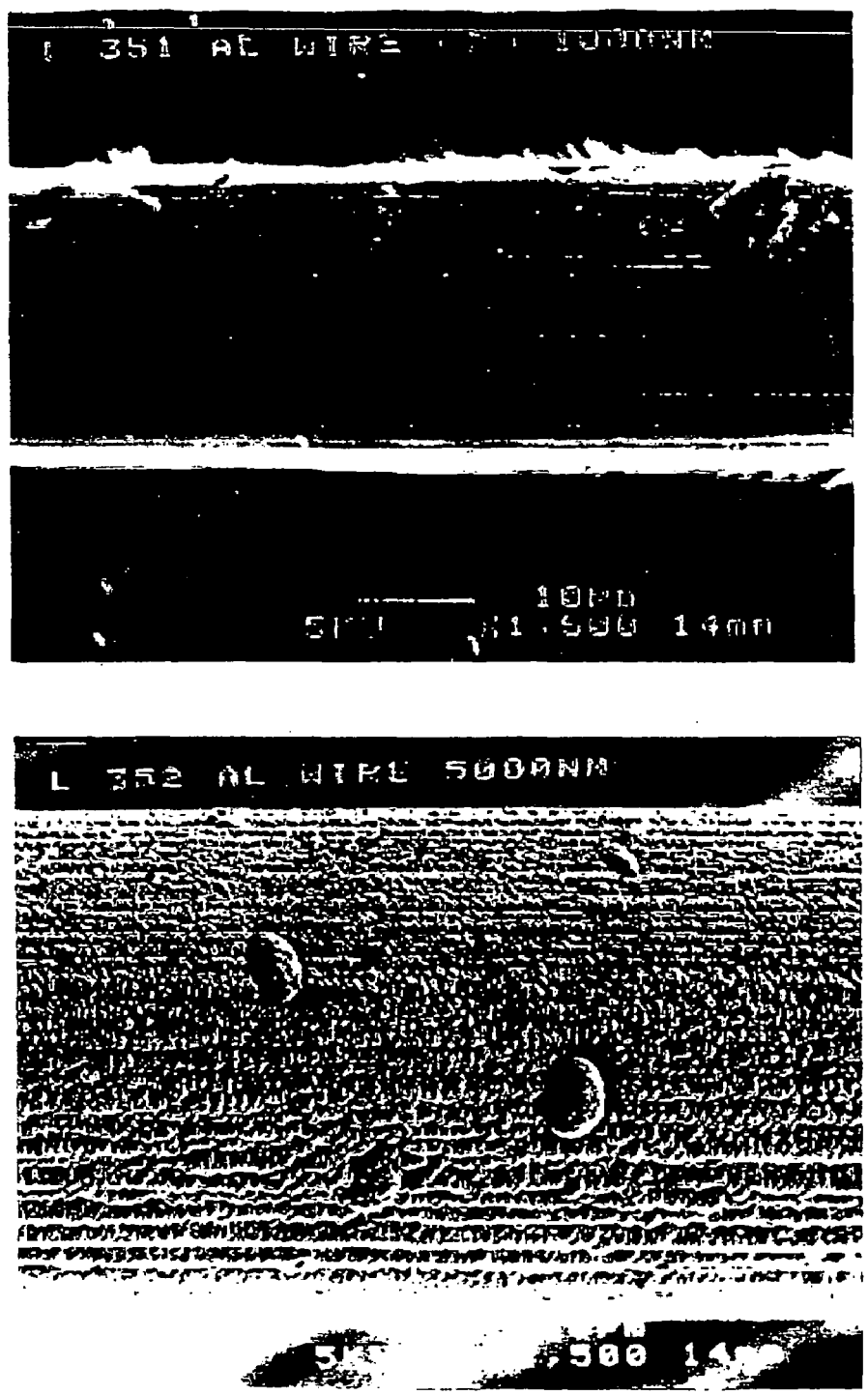
Figure 12:
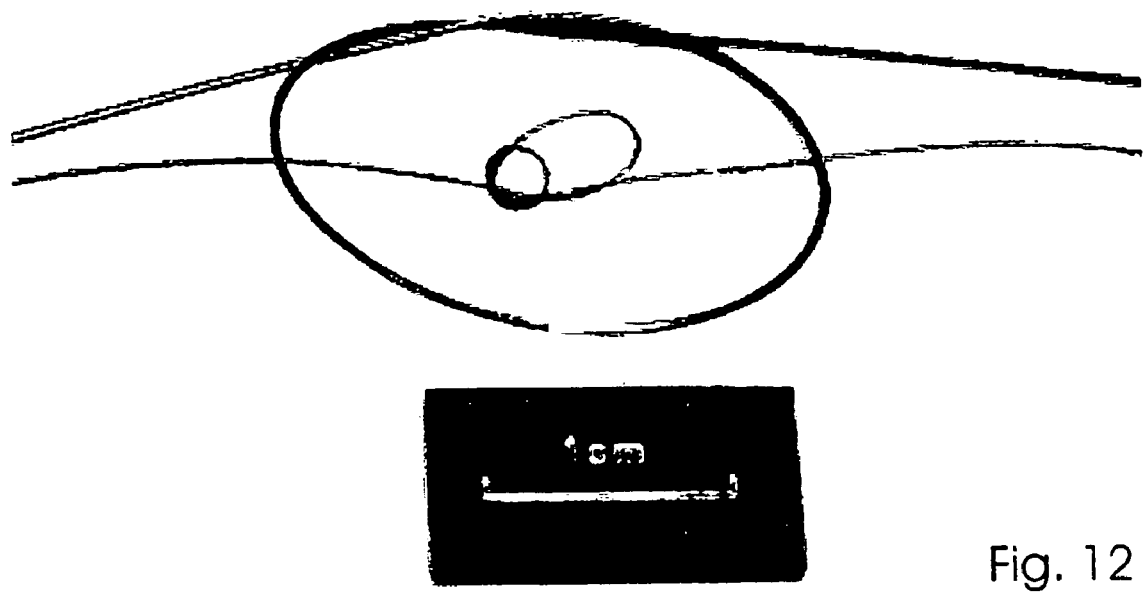

FIG. 10 is an enlarged view of polyester gauze fibres after stain etching (a,b) (scale shown) and (c) the EDX spectrum of the fibres, FIG. 11 shows a scanning electron microscope image of a silicon coated (a) biodegradable suture (b) aluminium wire and (c) hollow glass fibre, (scale shown) and FIG. 12 is an enlarged view of a coated suture and fibre illustrating the retained flexibility of the structure (scale shown).

EXAMPLE 1

Preparation of Extruded Poly-Si Fibres and Fabrics Obtained Therefrom

Poly Si microwires of diameter 5-25 micron diameter are first made by the "Taylor microwire process". Here, a poly or metallurgical grade silicon charge is melted inside a glass tube by a local heating source and fine wire drawn out through an orifice by mechanical pulling. The wire so produced is sheathed in silica which is removed by HF-based treatment.

The wires are then woven, knitted or braided into appropriate design prior to porosification in a HF-based solution. For 5-10 micron diameter wires, full porosification is achievable with stain-etching techniques. Anodisation of fabric made from low resistivity poly/single crystal silicon could alternatively be used, especially for thicker fibre networks.

EXAMPLE 2

Preparation of Reinforced Silicon Fibres

Bundles of silicon composite fibres, prepared for example as described in Example 1, can be processed into much tougher forms using resin bonding techniques used to convert highly brittle glass into extremely tough fibreglass. Although the resin used in fibreglass may itself be brittle, the interface between the silicon and the resin (as with the glass-resin interface) will act as an effective barrier to crack propagation across the bundle.

EXAMPLE 3

Preparation of Extruded Polymer/Si Powder Fibres

A readily extrudable polymer is first blended with porous silicon powder to form a composite that can still be processed into fibres at moderate temperatures. The level of silicon incorporation is between 1-10 wt % for inducing bioactivity, 10-60 wt % for improving yield strength and 60-90 wt % for conferring electrical conductivity to an insulating polymer, for example.

When a biodegradable polymer such as polylactic glycolic acid (PLGA) is used, the composite textile retains biodegradability. When an established textile material such as Dacron™ is used, the inclusion of pSi powder can be incorporated as one additional step in a commercial sequence. Where electrically conducting polymers such as polyaniline or polyacetylene are used, textiles obtained are not biodegradable but could be rendered surface-bioactive by low levels of silicon addition.

EXAMPLE 4

Preparation of Hollow Amorphous/Polysilicon Microfibres

Commercially available polymer/silica fibres of diameters in the range 20-200 micron with a hollow core of diameter in the range 5-100 micron is first coated along its length with amorphous/poly silicon. This can be achieved by pulling the fibre through a vacuum sputtering/CVD chamber and with deposition at room temperature/elevated temperature respectively. The low thermal stability of polymers restricts their coating to amorphous films which can be carried out at room temperature. The core of the fibre is then removed by soaking in a suitable solvent/HF-based solution.

Porosification can once again be by stain etching or anodisation. Since microcracks limit fibre strength, improved drying techniques like supercritical processing are beneficial.

EXAMPLE 5

Preparation of Micromachined Poly-Si Fibres

Ultrathin fibres can be realised by the repetitive use of standard silicon wafers that are repetitively subjected to surface oxidation, poly-Si deposition, micromachining and HF-induced release. Porosification is carried out by stain etching either before or after the HF-release step. The maximum fibre length is defined by wafer diameter and fibre cross-section by poly-Si layer thickness and mask design.

EXAMPLE 6

Silicon Incorporation into Preformed Fabric

Commercially available silicon powder (metallurgical grade or solar grade purity) is mechanically milled down to submicron particle size and then rendered porous by stain etching in an HF-based solution. The porous powder is then subjected to UV ozone treatment to generate surface hydroxyl groups. Their replacement by 3-chloropropyl (CP) groups is then achieved by using (3-chloropropyl) tri-methoxysilane (CP-TMS). Covalent binding via propyl ether linkages to commercially available fabric, such as cotton, linen or a synthetic fibre, is then achieved by co-incubation in boiling toluene. After sufficient reaction time (e.g. 2 hours at 110° C.) sonification can be used to remove physisorbed pSi powder, leaving only covalently linked silcon powder bound to the surface of the fabric.

EXAMPLE 7

Silicon Incorporation into Preformed Yarn

Non porous or porous silicon fibre prepared by the process described in Examples 1 or 5 is wrapped around textile fibres that have already been spun into yarn. This can provide an electrically conductive pathway within a fibre of predominantly standard textile material.

EXAMPLE 8

Metal Replacement by Silicon in Silk Organza

Silk organza is a finely woven silk fabric, originating from India, which combines gold, silver or copper with silk threads into a fabric that is anisotropically conductive. The warp consists of parallel silk threads. Through this warp, the weft is woven with a silk thread that has been wrapped in a metal foil helix.

In this embodiment however, low resistivity silicon fibres are used instead of the foil wrapped fibres. The spacing between the fibres results in a correctly orientated strip of the fabric functioning like a ribbon cable.

EXAMPLE 9

Preparation of Porous Silicon Fibre

Porous silicon fibre was obtained by cleaving a mesoporous film on wafers over a glass slide covered in filter paper. An 80% porosity and 64 micron thick film was fabricated from a (100) oriented p+ wafer (0.005±-20% ohm cm) made by anodisation at 100 milliamps per square centimetre, for 20 minutes in equal volumes of 40 wt % HF and pure ethanol. Upon scribing the back of the wafer along directions parallel or perpendicular to the "wafer flat" and then breaking over the aligned edge of a glass slide,some short (1-10 mms) fibres broke away from the diced chip. Examples are shown in FIG. 4 which show optical microscope images at ×200 magnification of fibres of rectangular cross-section (a) 95-100 micron width (b) 25-30 micron width. The fibrous structures are fully porous (80% porosity) and brown to the eye. FIG. 4(c) is another optical microscope image of the larger fibre bent on a carbon pad to illustrate its flexibility.

EXAMPLE 10

Preparation of Porous Silicon Fibre

In an alternative method, porous silicon fibre was obtained by etching and anodisation of sawn silicon comb-like structures like that shown in FIG. 5(a). The edge of a 3 inch diameter wafer was given a series of 45 cuts using a 75 micron wide blade with a pitch of 225 micron. This created an array of supported single crystal beams of approximate length 12 mms and rectangular cross-section 150×380 micron.

These beams were then subjected to ultrasonic cleaning in acetone and then an isotropic wet etch in 70% nitric acid, glacial acetic acid and 40% aqueous HF at a 5:1:1 volume ratio. This step removes saw damage and is used to define cross-sectional profile of fibres to be generated in the next step. The etching solution was continuously stirred and etch duration was 7.5 minutes for the data shown here. FIG. 5(b,c) shows the beam array in plan-view before and after such an etch where the width has been reduced from 145+/−5 micron to 25+/−5 micron. The wafer segment was then further cleaved into a narrower comb-like structure with no bulk silicon adjacent to the ends of the protruding beams, in preparation for anodisation. An anodic potential of 1.0 Volt was applied for 5 minutes in 40% aqueous HF/ethanol (1:1 by volume) between the suspended structure and a circular platinum crucible acting as the cathode. Only the lower half of the beams were immersed in the electrolyte. The resulting high current densities caused the psi films to delaminate as fibres of uniform width defined by beam dimensions and anodisation time.

As an alternative, it would be possible to initially apply low current densities and then a sufficiently high current density to cause "lift-off", as is well known in the production of pSi membranes from whole wafers.

FIG. 6(a-c) show examples of a 20 micron wide, a 4 micron wide and the end of a multistrand fibre respectively, obtained using this method. As a result of the anodisation conditions used, the porosity of these wholly porous structures is in excess of 60%.

EXAMPLE 11

Preparation of Woven Silicon Structures

The sawing and etching process described above was used to demonstrate the feasibility of weaving pure silicon fibres using larger structures. Square sections of wafers were sawn into comb-like structures and given etch treatments to reduce thickness to 300, 200 and 100 microns over much longer lengths.

FIG. 7(a) shows an example of a pure single crystal Si weave where both warp and weft fibres have 200 micron thickness. FIG. 7(b,c) shows a Si weave containing weft fibres of 300 microns and warp fibres of 100 microns thickness. The latter have a pSi coating derived by stain etching as described in Example 12 hereinafter, which gives them a brown colour to the eye.

EXAMPLE 12

Preparation of Si & Porous Si Coated Fabrics, Sutures and Threads

A range of fibrous materials were conformally coated with sputtered amorphous silicon in a modified Blazers Bak box coater equipped with four, 400×125 mm planar magnetrons arranged concentrically around a central substrate rotation stage. Coating was by sputtering from a 99.999% pure Si target doped with boron at $5 \times 10^{18}/cm^3$ with the target power set at 500 W, a base pressure of $10^{-8}$ torr, an ionisation atmosphere of $5 \times 10^{-3}$ torr of argon and a substrate temperature of 50 C. The substrates were rotated at speeds of between 0.0025 and 0.126 mm/sec and supported on a custom-built framework to improve uniformity and control thickness of coatings.

Figure 9C:
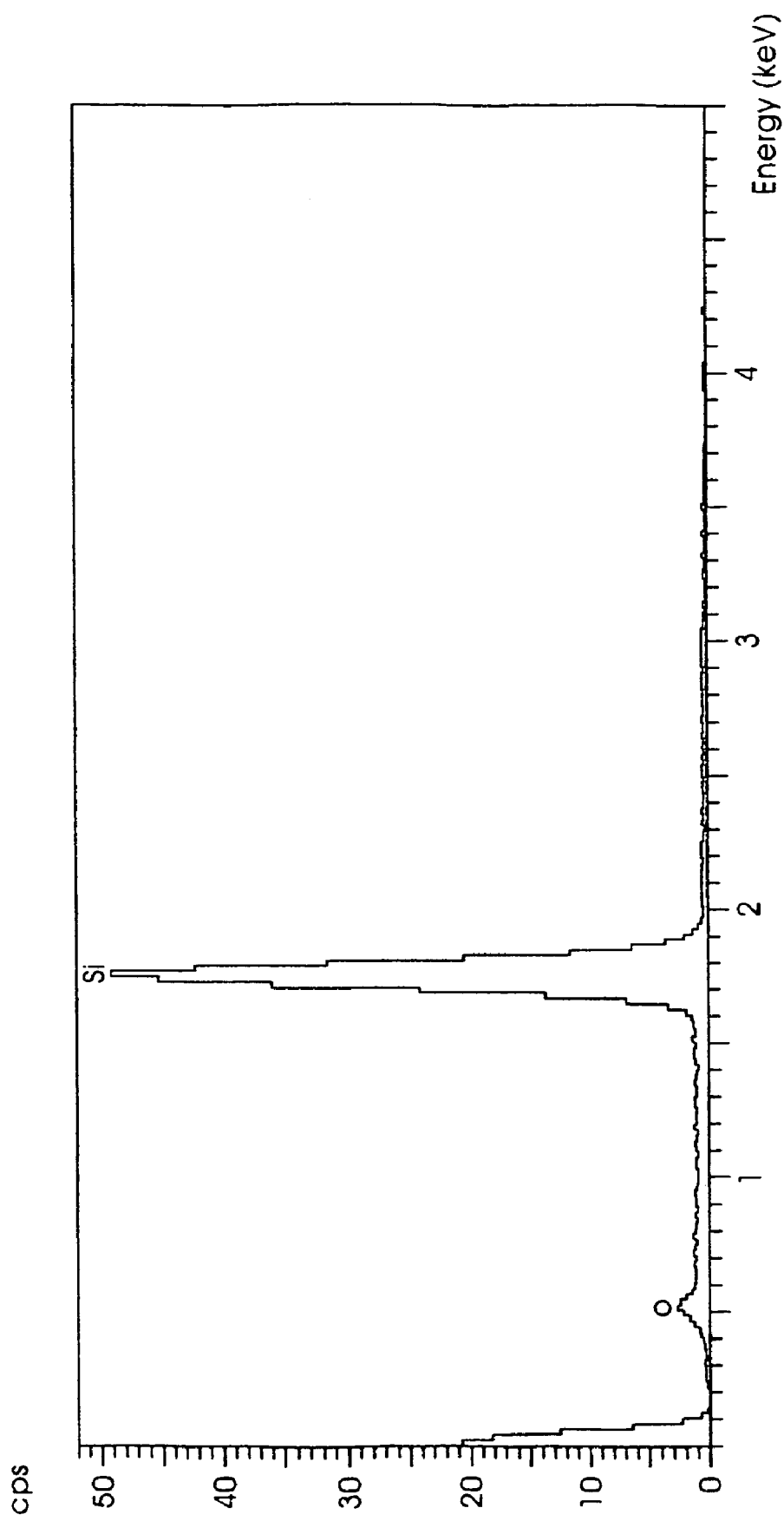

A commercially available polyester gauze (denier 100, mesh 156) was coated with 200 nm, 1 micron and 10 microns of silicon. FIG. 8(a,b) show segments of the gauze with the thickest coating and demonstrate the retained flexibility. The coatings were found to adhere well, even when tied into a knot as shown. FIG. 9(a,b) shows SEM images of part of the coated gauze and FIG. 9(c) the corresponding EDX spectrum showing a low level of oxygen in the coating.

Figure 10B:
Figure 10C:
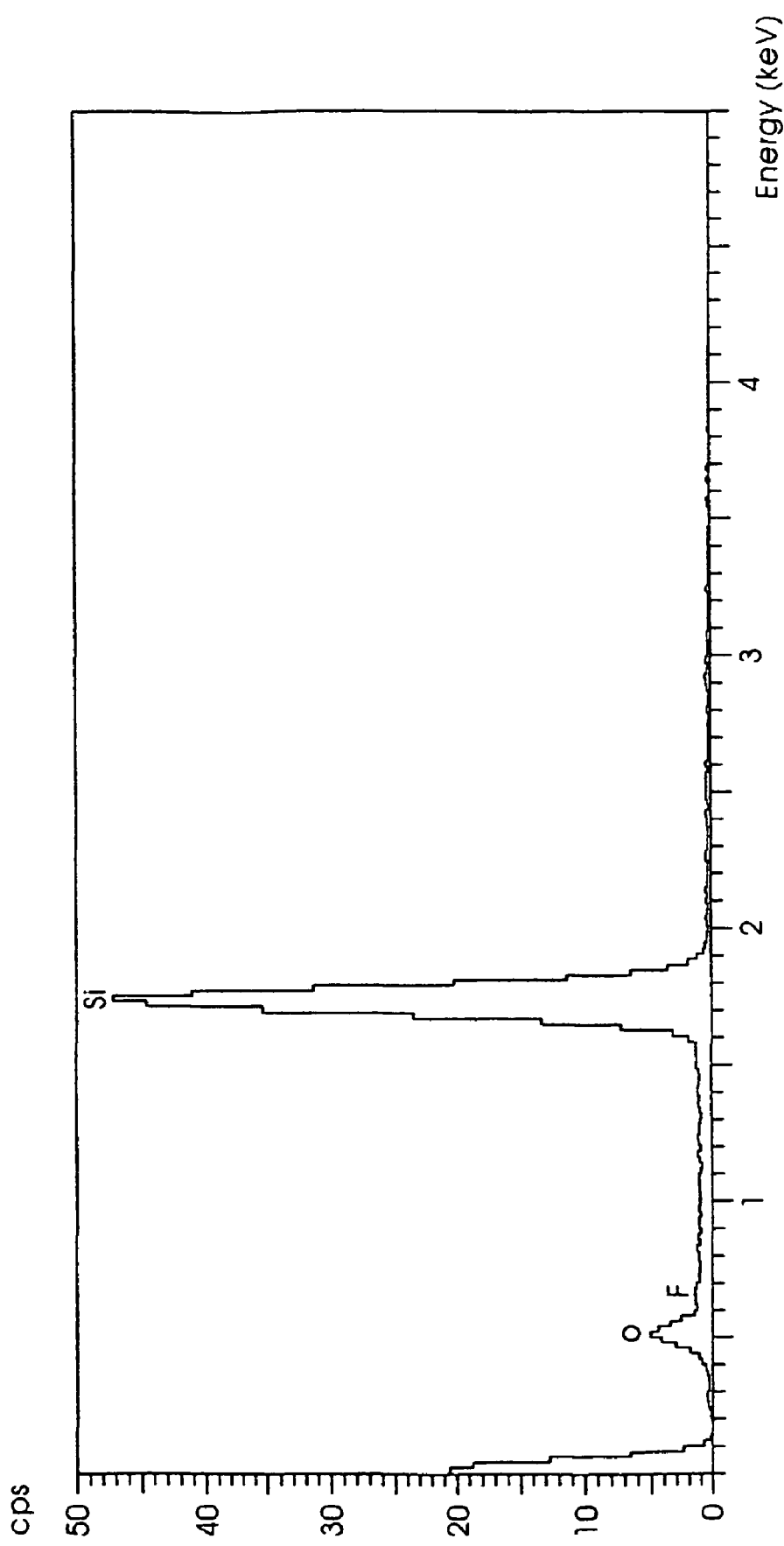

All exposed surfaces of the multistrand fibre network were found to have such a Si coating. FIG. 10(a,b,c) show the corresponding images and spectrum of the same gauze after partial porosification of the coating by stain etching. This was achieved by immersion of the fabric in a conventional stain etch solution containing 1 part by volume of 70% nitric acid to 100 parts by volume 40% HF for 60 seconds. A 90 second etch was found to cause partial delamination of the pSi coating. The porous nature of the coating is evident from the raised oxygen and fluorine levels in FIG. 10(c) and the presence of some cracks in FIG. 10(b).

Other examples of silicon coated structures include a biodegradable suture (the multifibre thread of FIG. 11(a)), a metal (aluminium) wire (FIG. 11(b)), hollow glass fibre and tubes (FIG. 11(c)) and other single strand polymer fibres. If desired, the glass or metal interior structures may subsequently be dissolved away using an appropriate solvent, such as hydrofluoric acid for glass, and hydrochloric acid for aluminium.

FIG. 12 is an optical image showing the flexibility of the suture and polymer fibres are maintained after Si coating.

EXAMPLE 12

Illustration of the Semiconducting Nature of Medical Fabrics Comprising Silicon

The woven pure silicon structure of FIG. 7(a) was rendered partially mesoporous by application of anodic electrical bias in equal volumes of 40% HF and ethanol. During and following this process the structure remained semiconductive since porous silicon is itself semiconducting.

The gauze coated with porosified silicon of FIG. 10 was cathodically biased in simulated body fluid. Prior to coating, the gauze is electrically insulating. Any current flow is thus restricted to the surface coating. This and the higher resistivity of the amorphous silicon compared with that of crystalline silicon resulted in a bias of 30 volts being needed to maintain a current flow of 1 mA through the fabric.

The conductivity of the gauze can be raised by using a more heavily doped ($10^{20}$ B/cm$^3$) Si target in the sputtering process, or by rendering the Si coating polycrystalline by laser annealing.

EXAMPLE 13

Preparation of Flexible Si Chains of Beads

Spherical polycrystalline Si granules of diameter 1-5 mm are commercially available in kg quantities from MEMC Inc, USA. After mechanical sieving these are size separated to for example 1.0 mm diameter. A 500 micron diameter hole is then drilled through each and batches given an isotropic chemical etch to remove drill damage. Subsequent linear alignment of holes is followed by threading, using a lead wire attached to the medical linking fibre. Partial porosification is achieved by stain etching or anodisation using a conducting Pt wire to link a chain of interconnected spheres.

EXAMPLE 14

Preparation of Flexible Si Chains of Microbeads

A silicon wafer is thermally oxidised and a 150 micron thick Si membrane bonded to that oxide surface. A linear array of rectangular trenches are then deep dry etched to a depth of 50 microns into that Si coating and in-filled with a spun-on resist. This step defines what will become the hollow core of every bead.

Following surface planarisation and cleaning, another 100 micron thick Si membrane is wafer bonded to the array. Photolithographically defined deep dry etching right through the Si-resist-Si structure to a depth of 250 microns is then carried out in a linear array pattern orthogonal to the resist channel direction. This step divides the linear Si columns into rows of aligned particles. The resist channels are then leached out by solvent and a suitable microwire (<50 micron diameter) threaded through at least one chain of aligned particles running across the wafer diameter.

When the entire array is suitably threaded the wafer is immersed in HF to dissolve the underlying oxide and release the particle chains. Isotropic etching can be subsequently used to remove sharp particle edges and stain etching to porosify the surfaces of every particle in the chain.

The invention claimed is:

1. A fabric for use as a medical fabric comprising porous silicon fibres, wherein the fabric has silicon microparticles incorporated therein.

2. A fabric according to claim 1 wherein the silicon microparticles are covalently bound to fibres of the fabric.

3. A fabric comprising porous silicon fibres, wherein the fabric is obtained by spinning, embroidery, weaving, knitting, braiding, fibre bonding, air-laying, wet laying, and/or laminating fibres.

4. A fabric comprising substantially pure porous silicon fibres of at least 100 cm in length.

5. A fabric comprising porous silicon fibres reinforced by resin bonding.

6. A fabric comprising porous silicon fibres wherein the fibres used in the fabric are less than 50 micron in diameter.

7. An electrically conductive porous silicon fabric which comprises silk warp threads and low resistivity porous silicon containing weft threads.

8. A porous silicon containing yarn wherein one or more pure porous silicon fibres are intertwined with textile fibres.

9. A porous silicon fibre comprising silicon beads connected together by means of a porous silicon resilient thread or wire wherein the silicon beads are of from 0.5 to 5 mm in diameter.

10. A porous silicon fibre according to claim 9 wherein said resilient thread or wire is a biodegradable suture.

11. A porous silicon fibre according to claim 9 wherein the silicon beads are from 10-500 microns in diameter.

12. A porous silicon fibre according to claim 9 wherein the silicon beads are porous.

* * * * *